United States Patent
Kelly et al.

(10) Patent No.: US 11,883,561 B1
(45) Date of Patent: Jan. 30, 2024

(54) DRUG ELUTING IMPLANTS AND METHODS FOR PRODUCING THE SAME

(71) Applicants: Reselute, Inc., Durham, NC (US); Duke University, Durham, NC (US)

(72) Inventors: Cambre Kelly, Durham, NC (US); Bijan Abar, Durham, NC (US); Jake Donovan, Durham, NC (US)

( * ) Notice: Subject to any disclaimer, the term of this patent is extended or adjusted under 35 U.S.C. 154(b) by 0 days.

(21) Appl. No.: 18/048,549

(22) Filed: Oct. 21, 2022

(51) Int. Cl.
  *A61L 27/44* (2006.01)
  *A61L 27/54* (2006.01)

(52) U.S. Cl.
  CPC ............. *A61L 27/44* (2013.01); *A61L 27/54* (2013.01); *A61L 2300/402* (2013.01); *A61L 2300/406* (2013.01); *A61L 2300/416* (2013.01)

(58) Field of Classification Search
  CPC ..... A61L 27/44; A61L 27/54; A61L 2300/402
  See application file for complete search history.

(56) References Cited

U.S. PATENT DOCUMENTS

| | | | | |
|---|---|---|---|---|
| 10,772,732 | B1* | 9/2020 | Miller | A61F 2/30771 |
| 2004/0249441 | A1* | 12/2004 | Miller | A61L 31/16 |
| | | | | 623/1.42 |
| 2005/0278025 | A1* | 12/2005 | Ku | A61F 2/3872 |
| | | | | 623/20.29 |
| 2006/0204548 | A1* | 9/2006 | Nivaggioli | A61K 9/0051 |
| | | | | 514/171 |
| 2009/0234459 | A1* | 9/2009 | Sporring | A61L 27/446 |
| | | | | 623/18.11 |
| 2015/0141549 | A1* | 5/2015 | Oshima | A01N 25/10 |
| | | | | 523/456 |

FOREIGN PATENT DOCUMENTS

WO   WO-2021072118 A1 * 4/2021 ........... B29C 64/129

OTHER PUBLICATIONS

Formlabs, Cimquest Inc., 2020, pp. 1-10 (Year: 2020).*
Safety Data Sheet, Form Labs, Feb. 4, 2022, pp. 1-12 (Year: 2022).*

* cited by examiner

*Primary Examiner* — Andrew S Rosenthal
*Assistant Examiner* — Lyndsey M Beckhardt
(74) *Attorney, Agent, or Firm* — Husch Blackwell LLP; Bryan D. Stewart; Arianne Rodriguez (57) ABSTRACT

A method for making a therapeutic agent-eluting temporary medical implant. In various embodiments, the method includes normalizing a quantity of therapeutic agent particles to attain a size distribution of 0.1-100 microns; creating a non-solid blend of a polymer and at least one therapeutic agent including between about 0.1 and about 20.0 weight percent of at least one therapeutic agent to a total weight of the non-solid blend; vat polymerizing the non-solid polymer blend to produce a therapeutic-eluting implant including at least one therapeutic agent homogenously distributed throughout; and cleaning and curing the therapeutic agent-eluting implant to produce a final device that supports physiologic loads when implanted within the patient. In at least one embodiment, the method includes of using a therapeutic agent that includes of one or more antibiotic, antifungal, analgesic, and/or chemotherapeutic.

1 Claim, 7 Drawing Sheets

DRUG ELUTING IMPLANTS AND METHODS FOR PRODUCING THE SAME

TECHNICAL FIELD

The present disclosure relates generally to processes for creating drug eluting implants.

BACKGROUND

The 2021 AJRR Annual Report reported 2.2 million primary and revision hip and knee arthroplasties between 2012 and 2020. It is expected that the number of total hip replacements and total knee replacements will increase. Hip and knee replacements can improve quality of life for patients. However, metal implants can have post-surgical complications including infection of the joint. Bacteria can form treatment-resistant biofilms on metal implant surfaces. This is known as periprosthetic joint infection (PJI).

PJI is treated by removal of infected hardware, debridement of the infected tissue, and antibiotic administration. The current standard of care in PJI for antibiotic delivery is a temporary cement antibiotic spacer. The spacer is made from polymethyl methacrylate (PMMA), a synthetic polymer, and gentamicin, a broad-spectrum antibiotic. Generally speaking, PMMA and gentamicin antibiotic spacers are created on a back table in an operating room, so dosing of gentamicin may be imprecise at best. In some instances, PMMA is dosed with a quantity of gentamicin that renders the PMMA structurally inadequate for the load-bearing applications for which it is designed. When the infection clears, the spacer is replaced with a new replacement implant.

Similarly, infection of the long bone or extremities, also known as osteomyelitis, is a devasting condition which can result from atraumatic or post-traumatic etiologies. In some cases, the affected anatomy is treated with internal fixation and delivery of local antibiotics from non-degradable bone cement (PMMA) or degradable carriers.

As a result, there is a long-felt, but unsolved need for improved antibiotic eluting implants (and like devices) and methods of producing and installing the same.

BRIEF SUMMARY OF THE DISCLOSURE

One aspect of the present disclosure generally relates to a method for producing a therapeutic agent-eluting medical implant (which may be temporary). In particular, the present disclosure relates to a method for producing a therapeutic agent-eluting temporary medical implant including a therapeutic agent integrated into a biocompatible photoresin, the resulting implant supporting physiologic loads when implanted within the patient.

According to a first aspect, a method for producing a temporary medical implant including: 1) creating a non-solid blend of a polymer and at least one therapeutic agent including between about 0.1 and about 20.0 weight percent of at least one therapeutic agent, wherein the weight percent is relative to a total weight of the non-solid blend; and 2) vat polymerizing the non-solid polymer blend containing at least one therapeutic agent to produce a therapeutic agent-eluting implant including the at least one therapeutic agent homogenously distributed throughout.

According to a second aspect, the method according to the first aspect or any other aspect, wherein the therapeutic agent includes one or more of the following: antibiotic, antifungal, analgesic, or chemotherapeutic.

According to a third aspect, the method according to the second aspect or any other aspect, further including normalizing a quantity of therapeutic agent particles to attain a size distribution of 0.1-100 microns.

According to a fourth aspect, the method according to the second aspect or any other aspect, further including normalizing a quantity of therapeutic agent particles to attain a size distribution of 30-40 microns.

According to a fifth aspect, the method according to the fourth aspect or any other aspect, further including cleaning and curing the therapeutic agent-eluting implant to produce a final device that supports physiologic loads when implanted within the patient.

According to a sixth aspect, the method according to the fifth aspect or any other aspect, wherein the therapeutic agent-eluting implant includes lattice structures.

According to a seventh aspect, the method according to the fifth aspect or any other aspect, wherein the therapeutic agent-eluting implant includes a gyroid structure.

According to an eighth aspect, the method according to the seventh aspect or any other aspect, wherein the therapeutic agent-eluting implant includes a yield stress greater than or equal to 52 MPa.

According to a ninth aspect, the method according to the eighth aspect or any other aspect, wherein the therapeutic agent-eluting implant includes an ultimate tensile strength of greater than or equal to 20 MPa.

According to a tenth aspect, the method according to the ninth aspect or any other aspect, wherein the therapeutic agent-eluting implant includes a Compressive Modulus of greater than or equal to 1000 MPa.

According to an eleventh aspect, the method according to the tenth aspect or any other aspect, wherein the therapeutic agent-eluting implant includes an arthroplasty spacer.

According to a twelfth aspect, the method according to the tenth aspect or any other aspect, wherein the therapeutic agent-eluting implant includes a fracture fixation device.

According to a thirteenth aspect, a therapeutic agent-eluting biocompatible implant including: 1) a homogenous photo-curable mixture including about 0.1 to about 20.0 weight percent of at least one therapeutic agent; 2) one or more lattice and/or cylindrical structures; 3) an ultimate tensile strength greater than or equal to 20 MPa; and 4) a Compressive Modulus of greater than or equal to 1000 MPa, wherein the therapeutic agent-eluting implant is mechanically stable when implanted within the patient.

According to a fourteenth aspect, the therapeutic agent-eluting biocompatible implant of the thirteenth aspect or any other aspect, wherein the therapeutic agent-eluting implant is temporary and includes a knee arthroplasty spacer.

According to a fifteenth aspect, the therapeutic agent-eluting biocompatible implant of the thirteenth aspect or any other aspect, wherein the therapeutic agent-eluting implant is temporary and includes a shoulder arthroplasty spacer.

According to a sixteenth aspect, the therapeutic agent-eluting biocompatible implant of the thirteenth aspect or any other aspect, wherein the therapeutic agent-eluting implant is temporary and includes a hip arthroplasty spacer.

According to a seventeenth aspect, the therapeutic agent-eluting biocompatible implant of the thirteenth aspect or any other aspect, wherein the therapeutic agent-eluting implant is temporary and includes an ankle arthroplasty spacer.

According to an eighteenth aspect, the therapeutic agent-eluting biocompatible implant of the thirteenth aspect or any other aspect, wherein the therapeutic agent-eluting implant is temporary and includes an elbow arthroplasty spacer.

According to a nineteenth aspect, the therapeutic agent-eluting biocompatible implant of the thirteenth aspect or any other aspect, wherein the therapeutic agent-eluting implant is temporary and includes a temporary intermedullary fracture fixation device.

According to a twentieth aspect, the therapeutic agent-eluting biocompatible implant of the thirteenth aspect or any other aspect, wherein the therapeutic agent-eluting implant is temporary and includes a temporary internal fracture fixation device.

According to a twenty-first aspect, the therapeutic agent-eluting biocompatible implant of the thirteenth aspect or any other aspect, wherein the therapeutic agent includes of one or more antibiotic.

According to a twenty-second aspect, the therapeutic agent-eluting biocompatible implant of the thirteenth aspect or any other aspect, wherein the therapeutic agent includes of one or more antifungal.

According to a twenty-third aspect, the therapeutic agent-eluting biocompatible implant of the thirteenth aspect or any other aspect, wherein the therapeutic agent includes of one or more analgesic.

According to a twenty-fourth aspect, the therapeutic agent-eluting biocompatible implant of the thirteenth aspect or any other aspect, wherein the therapeutic agent includes of one or more chemotherapeutic.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

DETAILED DESCRIPTION

Whether or not a term is capitalized is not considered definitive or limiting the meaning of a term. As used in this document, a capitalized term shall have the same meaning as an uncapitalized term is intended. However, the capitalization or lack thereof within the remainder of this document is not intended to be necessarily limiting unless the context clearly indicates that such limitation is intended.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

According to particular embodiments, the methods, devices, and systems herein are directed to a process for producing a therapeutic agent-eluting temporary medical implant including: 1) normalizing a quantity of therapeutic agent particles to attain a size distribution of 0.1-100 microns; 2) creating a non-solid blend of a polymer and at least one therapeutic agent including between about 0.1 and about 20.0 weight percent of at least one therapeutic agent to a total weight of the non-solid blend; 3) vat polymerizing the non-solid polymer blend to produce a therapeutic-eluting implant including at least one therapeutic agent homogenously distributed throughout; and 4) cleaning and curing the therapeutic agent-eluting implant to produce a final device that supports physiologic loads when implanted within the patient.

This process results in a therapeutic agent-eluting temporary medical implant device that supports physiologic loads when implanted within the patient. The resulting therapeutic agent-eluting implant has a yield stress greater than or equal to 52 MPa and an ultimate tensile strength of greater than or equal to 20 MPa, as well as a Compressive Modulus of greater than or equal to 1000 MPa. As will be understood, the therapeutic agent-eluting implant device may be a temporary or permanent implant. Further, the therapeutic agent-eluting implant devices discussed herein may be any suitable implant devices, including, but not limited to temporary spacers (for hips or knees), internal fracture or arthroplasty devices, intramedullary fixation devices, pins, screws, staples, and/or implants for shoulders, ankles, feet, hands, knees, hips, long bones (e.g., femur), short bones (e.g., tarsal bones of the foot or carpal bones of the hands), and spine.

As will be understood by one of ordinary skill in the art, "supports physiologic loads," as used herein may refer to implants that can withstand weight bearing or lifting by a human or animal.

As will be understood by one of ordinary skill in the art, "photoresin," or "photopolymer resin" as used herein may refer to a polymer which changes its properties upon exposure to radiation.

As will be understood by one of ordinary skill in the art, "biocompatible," as used herein may refer to compatibility with living tissue by not being overly or substantially toxic, injurious, or physiologically reactive and/or not causing substantial immunological rejection.

As will be understood by one of ordinary skill in the art, any suitable materials may be used in the processes and implants described herein. In at least one embodiment, the polymer in the above process is a biocompatible acrylic photopolymer resin. In one or more embodiments, the therapeutic agent in the above exemplary process is at least one antibiotic. In one or more embodiments, the therapeutic agent in the above exemplary process is at least one antifungal. In one or more embodiments, the therapeutic agent in the above exemplary process is at least one analgesic. In one or more embodiments, the therapeutic agent in the above exemplary process is at least one chemotherapeutic.

Exemplary Process

Figure 1:
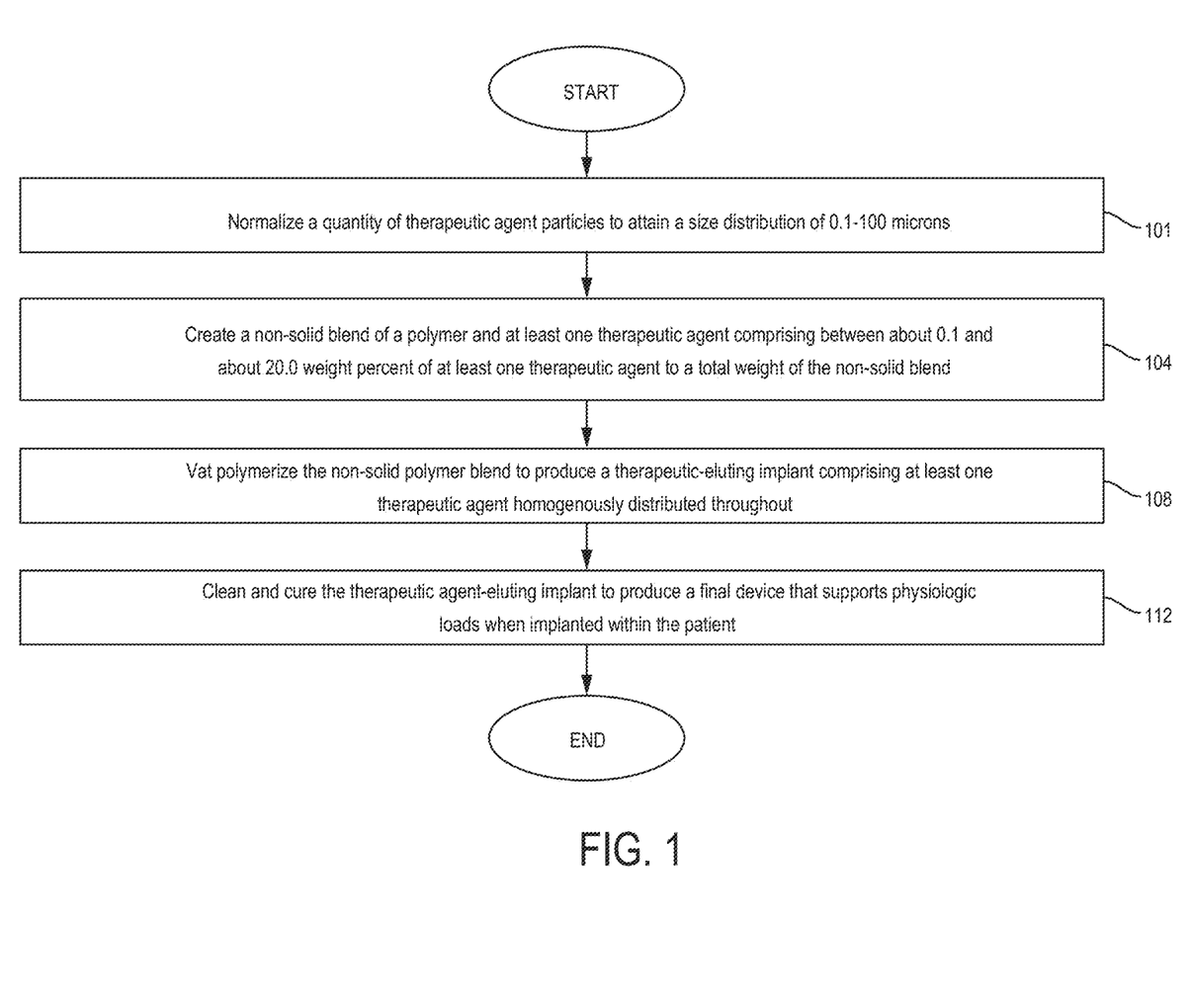
FIG. 1 is an exemplary process for creating a therapeutic agent-eluting medical implant, according to one embodiment.

Turning now to FIG. 1, an exemplary process for producing a therapeutic agent-eluting implant is shown. In at least one embodiment, the process includes: normalizing a quantity of therapeutic agent particles to attain a size distribution of 0.1-100 microns 101; creating a non-solid blend of a polymer and at least one therapeutic agent comprising between about 0.1 and about 20.0 weight percent of at least one therapeutic agent to a total weight of the non-solid blend 104; vat polymerizing the non-solid polymer blend to produce a therapeutic-eluting implant comprising at least one therapeutic agent homogenously distributed throughout 108; cleaning and curing the therapeutic agent-eluting implant to produce a final device that supports physiologic loads when implanted within the patient 112.

According to particular embodiments, this exemplary process begins at 101 by normalizing a quantity of therapeutic agent particles to attain a size distribution of 0.1-100 microns. In some embodiments, the size distribution is between about 30-40 microns. In at least one embodiment, the size distribution is between about 10-30 microns. In one or more embodiments, the size distribution is between about 40-100 microns. In further embodiments, the size distribution is between about 0.1-1.0 microns or less than 1.0 microns. In still further embodiments, the size distribution is greater than 100 microns. As will be understood from discussions herein, particle size distribution may be measured using various methods known to those skilled in the art including but not limited to Laser Diffraction (LD), Dynamic Light Scattering (DLS), Dynamic Image Analysis (DIA) or Sieve Analysis.

In various embodiments, normalizing the quantity of therapeutic agent particles includes pulverizing the therapeutic agent into a fine powder. In at least one embodiment, normalizing the quality of therapeutic particles includes grinding or crushing the therapeutic agent via mill or like device. According to particular embodiments, normalizing the quality of therapeutic agent includes pulverizing the therapeutic agent into a fine powder, then sifting or otherwise isolating certain sizes (e.g., particles of a size between about 30-40 microns) of the pulverized therapeutic agent.

In some embodiments, the therapeutic agent is an antibiotic (e.g., broad spectrum). In at least one embodiment, the therapeutic agent includes one or more of an antibiotic, antifungal, analgesic, or chemotherapeutic.

At 104, the process continues with creating a non-solid blend of a polymer and at least one therapeutic agent including between 0.1 and about 20.0 weight percent of at least one therapeutic agent to a total weight of the non-solid blend. In various embodiments, the polymer may be any suitable material. It can be one polymer or a blend. In various embodiments, the polymer is any suitable biocompatible photoresin such as Accura ClearVue, MED-WHT 10, Rigid White, BioTough D70 MF ULWA, BIORES RED, BIORES Micro Precision, E-Guide, E-Shell, BioMed Amber, BioMed Clear, Biomed White, Biomed Black.

In various embodiments, the biocompatible polymer includes various weight percent ratios of the following ingredients: esterification products of 4,4'-isopropylidenediphenol, ethoxylated and 2-methylprop-2-enoic acid, urethane dimethacrylate, methacrylate monomer(s), and photoinitiator(s). In at least one embodiment, the biocompatible polymer has an initial boiling point/range of >200° C., a closed cup flash point of >100° C., a density of about 1.00-1.50 g/cm$^3$, a dynamic viscosity of 1300-1450 cps at 25° C., and is not flammable, According to at least one embodiment, the biocompatible polymer has the following formulation: 50-70% of esterification products of 4,4'-isopropylidenediphenol, ethoxylated and 2-methylprop-2-enoic acid, 25-45% urethane dimethacrylate, 7-10% methacrylate monomer(s), and <2% of photoinitiator(s), has an initial boiling point/range of >100° C., a closed cup flash point of >93.5° C., a density of 1.09 g/cm$^3$, a dynamic viscosity of 1350 cps at 25° C., and is not flammable.

As will be understood from discussions herein, the homogenous non-solid blend of therapeutic agent and polymer can be achieved using homogenization with an emersion blender or homogenizer. As will also be understood from discussions herein, the non-solid blend of therapeutic agent and polymer (or multiple polymers) may include a non-homogenous blend, where, for example, only portions of the polymer are doped or mixed with a therapeutic agent such that when the blend is formed into a device, portions of the device are strategically doped with the therapeutic agent.

In various embodiments, the therapeutic agent can include one or more antibiotic, antifungal, analgesic, or chemotherapeutic. In various embodiments, an antibiotic may be any compound which inhibits the growth of or destroys bacteria. Examples include, but are not limited to, gentamicin, penicillin, amoxicillin, azithromycin, tobramycin, vancomycin, doxycycline, cephalexin, ciprofloxacin, clindamycin, metronidazole, or sulfamethoxazole and trimethoprim.

In some embodiments, an antifungal may be any compound which inhibits the growth of or destroys fungi. Examples include but are not limited to clotrimazole, econazole, voriconazole, miconazole, terbinafine, fluconazole, ketoconazole, nystatin, or amphotericin.

In one or more embodiments one or more analgesic may be any compound which relieves pain or is a painkiller Examples include but are not limited to NSAIDS, acetaminophen, aspirin, ibuprofen, naproxen, celecoxib, diclofenac, fenoprofen, indomethacin, ketoprofen, tolmetin, diflunisal, flurbiprofen; or opioids (narcotics) including hydrocodone, oxycodone, oxymorphone, morphine, codeine, or fentanyl.

In at least one embodiment, a chemotherapeutic may be any compound which stops the growth of cancer cells, either by killing the cells or by preventing them from dividing. Examples include but are not limited to cyclophosphamide, chlorambucil, paclitaxel, methotrexate, carboplatin, pemetrexed, vincristine, docetaxel, doxorubicin, daunorubicin.

In various embodiments, the optimal amount concentration of the therapeutic agent is about 0.1 to about 20 weight percent which is then added to the polymer blend. However, the present disclosure is not limited to these concentrations. The concentration of therapeutic agent may be about 0.05 to 0.1 weight percent or greater or less than 20 weight percent.

Figure 2:
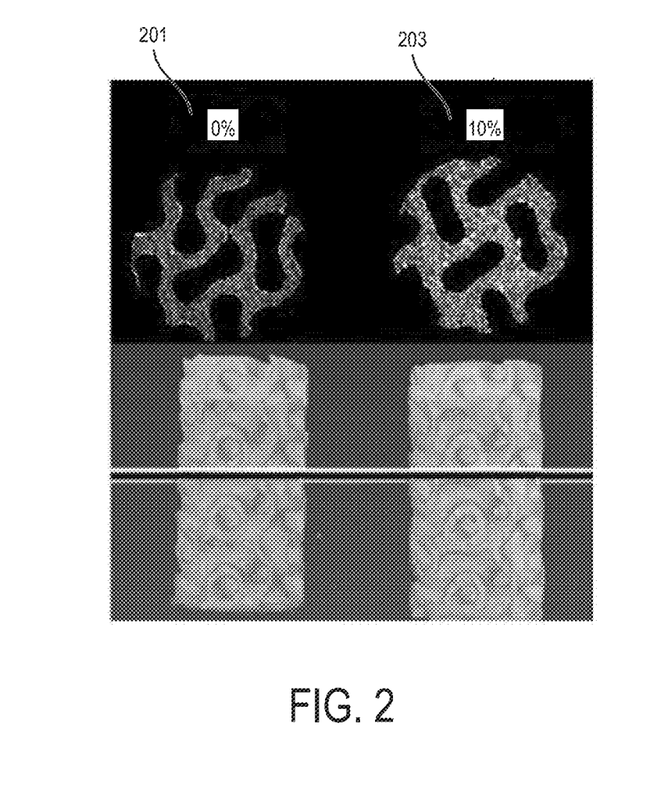
FIG. 2 illustrates an exemplary 3D printed structure, according to one embodiment.
Figure 3:
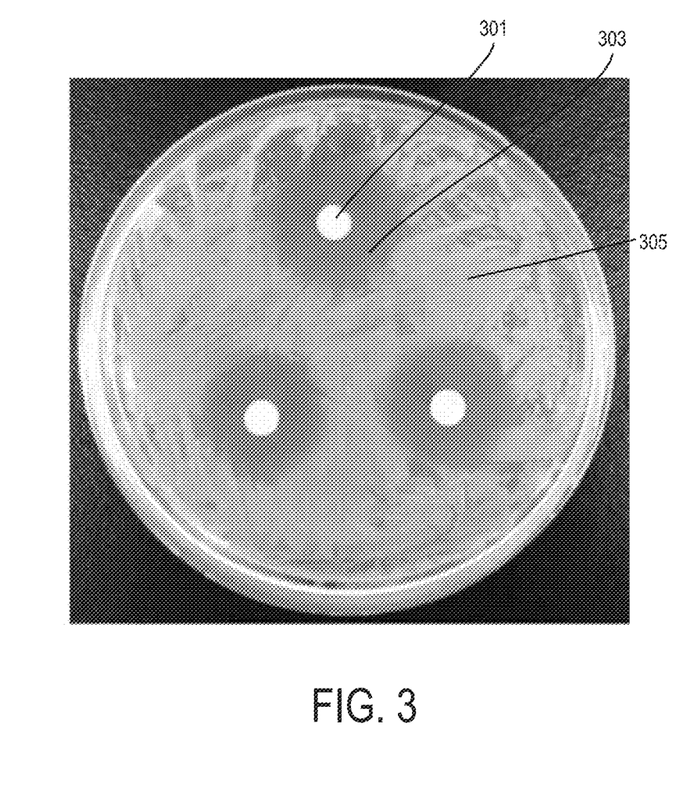
FIG. 3 illustrates discs soaked in elution from a printed cylinder made with gentamicin doped resin, according to one embodiment.

At 108, the process continues with vat polymerization of the non-solid polymer blend to produce a therapeutic-eluting implant including at least one therapeutic agent homogenously distributed throughout. In various embodiments, a computer-aided design (CAD) model of the 3D implant is sliced into thin 2D layers and uploaded onto a printer prior to layer wise vat polymerization to produce an implant appropriate for the patient's anatomy. In a particular embodiment as shown in FIG. 2, a non-solid blend of polymer and 10% weight percent gentamicin blended with a biocompatible photopolymer resin can be used in printing of complex structures including gyroid cylinder shapes 203 in a similar fashion to the same polymer without gentamicin 201. In a particular embodiment, the non-solid polymer blend mixed with the therapeutic agent can be fabricated by vat photopolymerization into a shape including lattice structures. In a particular embodiment, the non-solid polymer blend mixed with the therapeutic agent can be fabricated by vat photopolymerization into a shape including a gyroid structure. Additionally, in at least one embodiment, the optimal weight % of therapeutic agent, results in a functional elution of the therapeutic agent. As shown in FIG. 3, discs 301, soaked in elution from a printed cylinder made with gentamicin doped resin, create a zone of inhibition 303 when placed on a petri dish coated with *E. coli* 305. This zone of inhibition shows that a particular embodiment has an elution of antibiotic necessary for an inhibitory effect.

Figure 4:
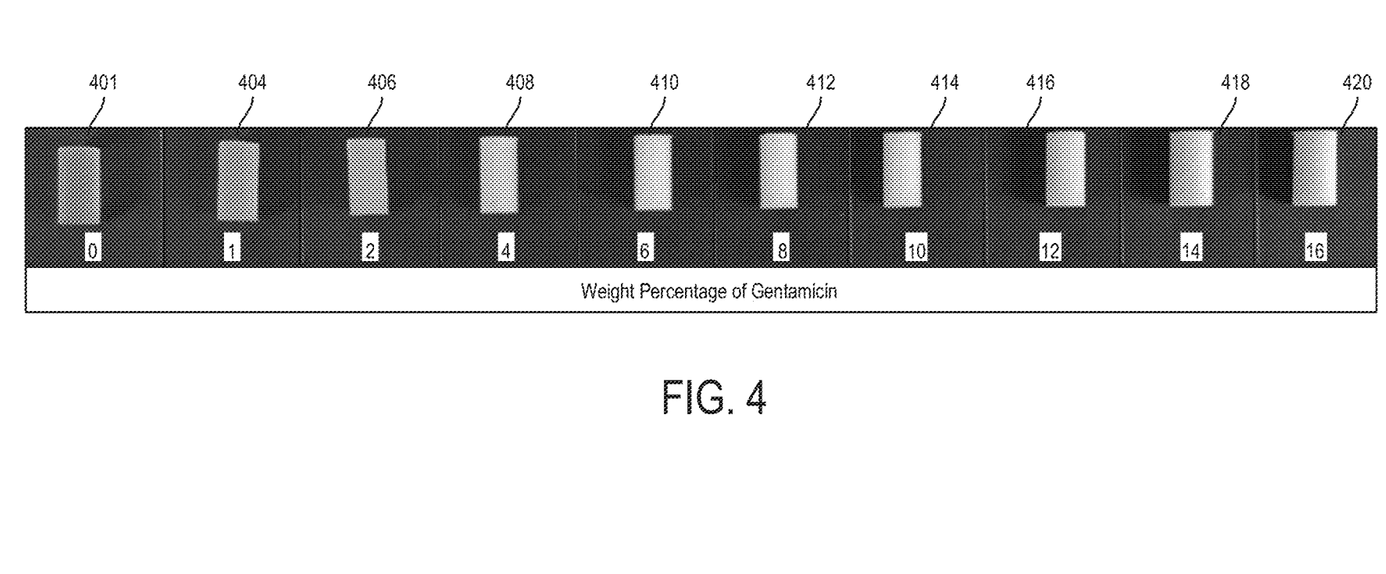
FIG. 4 illustrates exemplary 3D printed cylinders with varying wt/wt % s of gentamicin, according to one embodiment.

In particular embodiments, as shown in FIG. 4, gentamicin can be incorporated into a biocompatible photopolymer resin at weight percentages of 1-16% and printed into cylinders. FIG. 4 illustrates printed cylinders containing 0% 401, 1% 404, 2% 406, 4% 408, 6% 410, 8% 412, 10% 414, 12% 416, 14% 418, and 16% 420 wt/wt percent of gentamicin.

At 112, the process continues with cleaning and curing the therapeutic agent-eluting implant to produce a final device that supports physiologic loads when implanted within the patient. In particular embodiments, the product is washed in isopropyl alcohol (IPA) and cured under UV light and heat. In various embodiments, the final device includes an arthroplasty spacer or fracture fixation device. In one or more embodiments the final device includes a temporary knee, shoulder, hip, ankle, or elbow arthroplasty spacer. In one or more embodiments the final device includes an intermedullary or extramedullary fracture fixation device.

Exemplary Mechanical Data

Figure 5:
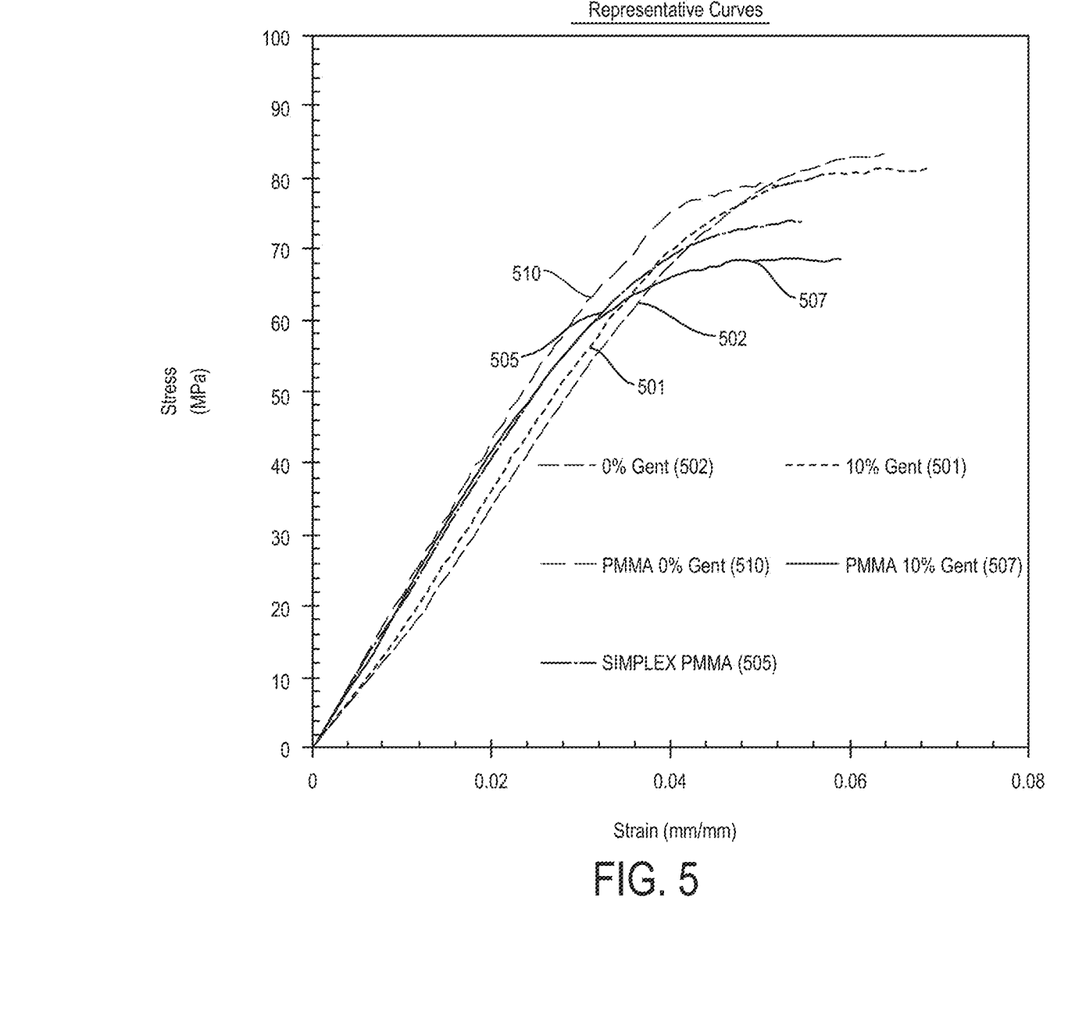
FIG. 5 is an exemplary stress-strain graph showing compressive strength of 10% wt/wt gentamicin doped PMMA and a biocompatible photopolymer resin, according to one embodiment.

FIGS. 5-7D show exemplary compressive yield strength for gentamicin-eluting temporary medical implants. FIG. 5 depicts poly(methyl methacrylate) (PMMA) and a biocompatible photopolymer resin fabricated by vat photopolymerization into cylinders with and without added antibiotics. FIG. 5 illustrates that the addition of 0.82% wt/wt gentamicin to a commercially available premixed SIMPLEX PMMA bone cement blend decreases the compressive yield strength in the resulting printed cylinder 505 as well as PALCOS PMMA bone cement doped with 10% wt/wt gentamicin 507 compared to the PMMA undoped control 510. In contrast, the addition of 10% wt/wt gentamicin 501 to a biocompatible photopolymer resin blend did not significantly reduce compressive properties compared to the undoped biocompatible photopolymer resin 502. For example, as shown in FIG. 5, doping SIMPLEX PMMA and PALCOS PMMA resulted in a decrease in compressive properties of at least 14%, where doping a biocompatible photopolymer resin resulted in on a minor reduction of compressive properties (e.g., less than 12%).

Figure 6:
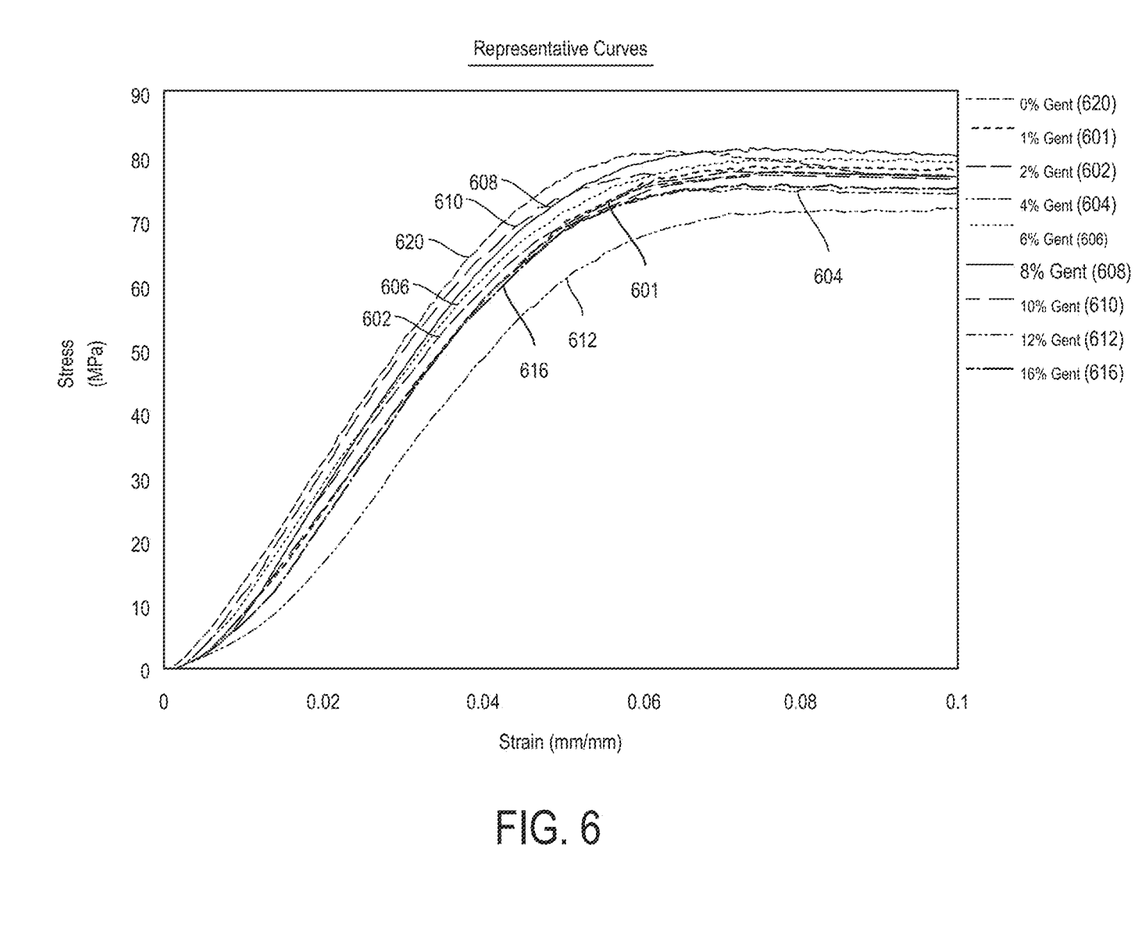
FIG. 6 is an exemplary line graph showing compressive strength of varying wt/wt % gentamicin doped biocompatible photopolymer resin, according to one embodiment.

Further, as shown in FIG. 6, compressive strength of the gentamicin doped biocompatible photopolymer resin is comparable to the undoped PMMA printed cylinders. FIG. 6 depicts the compressive strength of gentamicin doped biocompatible photopolymer resin printed cylinders containing 1% 601, 2% 602, 4% 604, 6% 606, 8% 608, 10% 610, 12% 612, 16% 616 wt/wt gentamicin compared to 0% wt/wt a biocompatible photopolymer resin 620. FIG. 6 shows that addition of gentamicin in concentrations ranging from 1-16 wt/wt % to a biocompatible photopolymer resin does not decrease the compressive yield strength by more than about 12% of the resulting printed cylinder compared to the undoped biocompatible photopolymer resin control 620.

FIGS. 7A-7D show exemplary Compressive Modulus 700A, yield stress 700B, yield strain 700C, and ultimate stress 700D by concentration wt/wt % for cylinders fabricated by vat photopolymerization from a biocompatible photopolymer resin blend doped with various wt/wt precents of gentamicin.

Figure 7A:
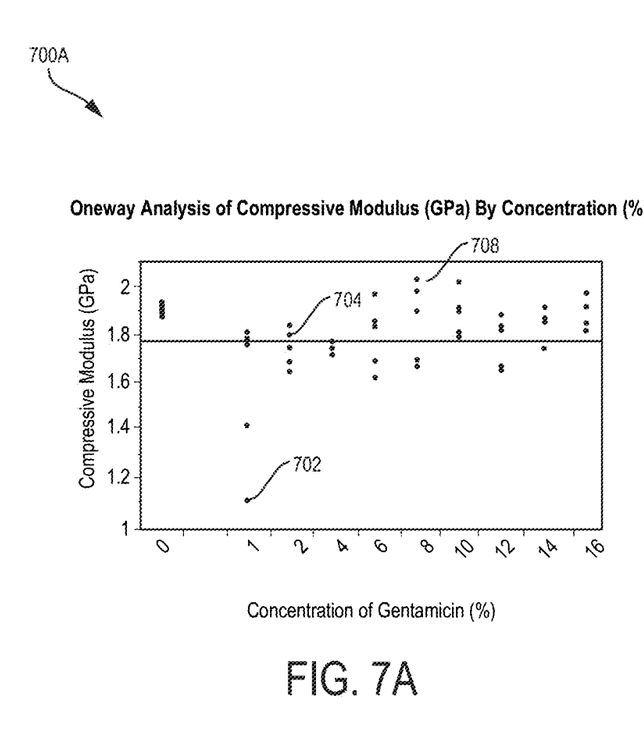
FIG. 7A-D are an exemplary plot graphs showing Compressive Modulus 700A, yield stress 700B, yield strain 700C, and ultimate stress 700D of varying wt/wt % gentamicin doped biocompatible photopolymer resin, according to one embodiment.

FIG. 7A illustrates that in various embodiments, the printed cylinders with various wt/wt percents of gentamicin resulted in properties with a range of Compressive Modulus from about 1000 MPa 702 to about 2000 MPa 708, with an average Compressive Modulus of about 1800 MPa 704. In 700A, various embodiments have a minimum Compressive Modulus of about 1000 GPa 702, an average Compressive Modulus of about 1800 GPa 704, and a maximum Compressive Modulus of about 2000 MPa 708.

Figure 7B:
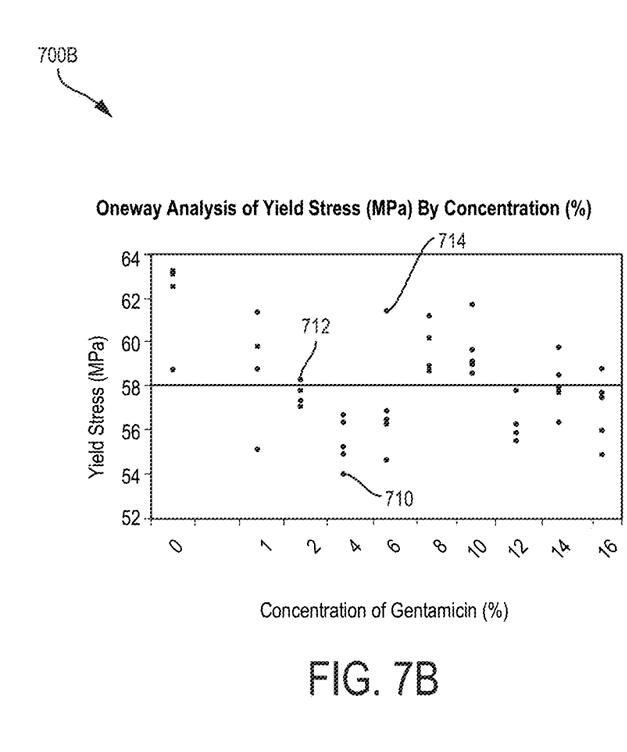

FIG. 7B illustrates that in various embodiments, the printed cylinders with various wt/wt percents of gentamicin resulted in properties with a range of yield stress from about 54 MPa 710 to about 62 MPa 714, with an average yield stress of about 58 MPa 712. In 700B, various embodiments have a minimum yield stress of about 54 MPa 710 (although minimum yield stress could be as low as 50 MPa), an average yield stress of about 58 MPa 712, and a maximum yield stress of about 62 MPa 714.

Figure 7C:
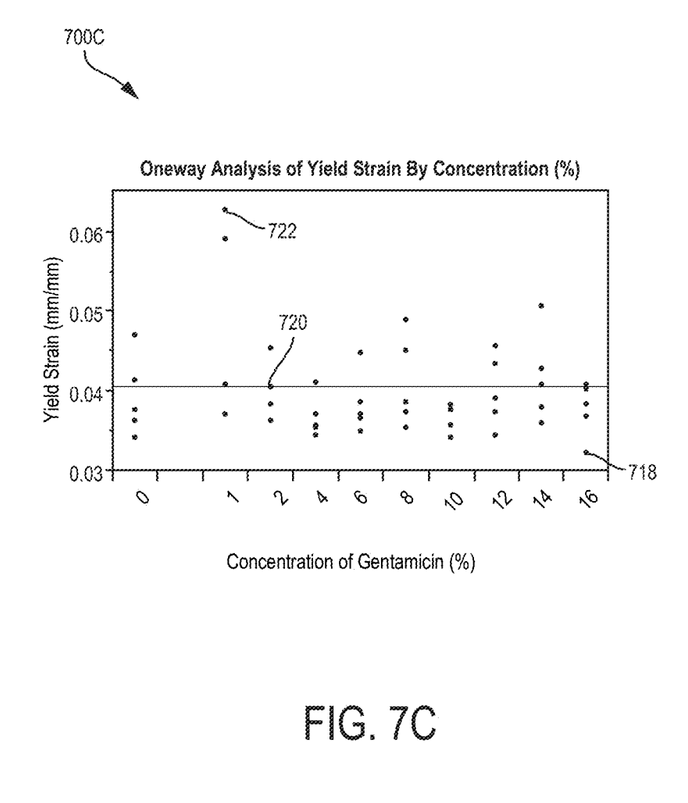

FIG. 7C illustrates that in various embodiments, the printed cylinders with various wt/wt percents of gentamicin resulted in properties with a range of yield strain from about 0.03 mm/mm 718 to about 0.065 mm/mm 722, with an average yield strain of about 0.04 mm/mm 720. In 700C, various embodiments have a minimum yield strain of about 0.03 mm/mm 718, an average yield strain of about 0.04 mm/mm 720, and a maximum yield strain of about 0.06 mm/mm 722.

Figure 7D:
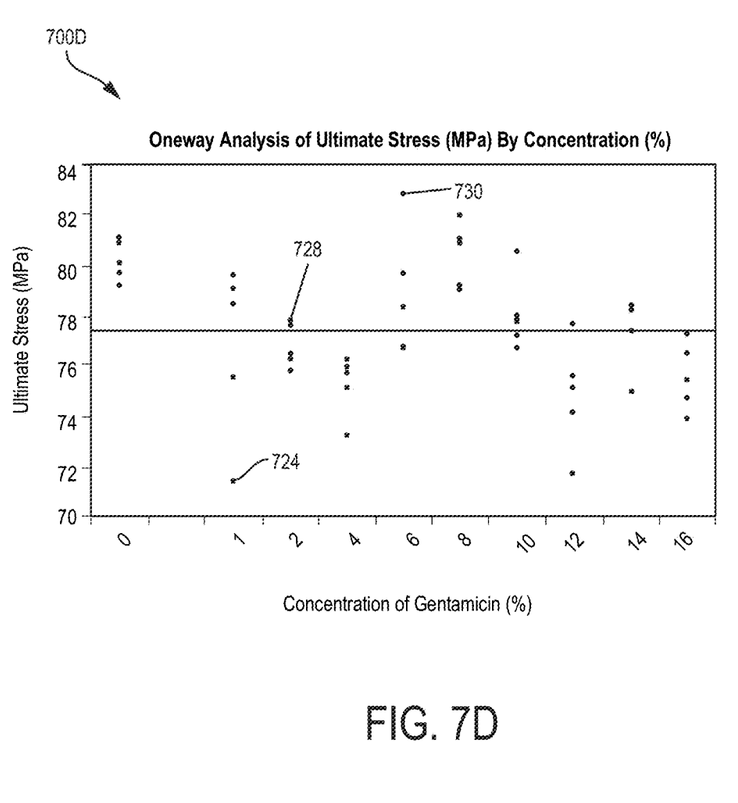

FIG. 7D illustrates that in various embodiments, the printed cylinders with various wt/wt percents of gentamicin resulted in properties with a range of ultimate stress from about 71 MPa 724 to about 83 MPa 730, with an average ultimate stress of about 77.5 MPa 728. In 700D, various embodiments have a minimum ultimate stress of about 71 MPa 724, an average ultimate stress of about 77 MPa 728, and a maximum ultimate stress of about 83 MPa 730.

TABLE 1

| % Gentamicin | Compressive Modulus (GPa) | | Yield Strength (MPa) | |
| --- | --- | --- | --- | --- |
| | Mean (SD) | Median [Min, Max] | Mean (SD) | Median [Min, Max] |
| 0% | 1.91 (0.0203) | 1.91 [1.88, 1.93] | 62.1 (1.91) | 63.0 [58.7, 63.2] |
| 1% | 1.57 (0.307) | 1.76 [1.10, 1.80] | 58.7 (2.29) | 58.7 [55.1, 61.3] |
| 2% | 1.74 (0.0807) | 1.75 [1.64, 1.83] | 57.5 (0.484) | 57.2 [57.0, 58.2] |
| 4% | 1.74 (0.0265) | 1.74 [1.71, 1.77] | 55.4 (1.12) | 55.2 [53.9, 56.7] |

TABLE 1-continued

| % Gentamicin | Compressive Modulus (GPa) | | Yield Strength (MPa) | |
|---|---|---|---|---|
| | Mean (SD) | Median [Min, Max] | Mean (SD) | Median [Min, Max] |
| 6% | 1.79 (0.137) | 1.83 [1.62, 1.97] | 57.1 (2.54) | 56.4 [54.6, 61.3] |
| 8% | 1.85 (0.166) | 1.90 [1.67, 2.03] | 59.5 (1.13) | 58.8 [58.6, 61.1] |
| 10% | 1.88 (0.0925) | 1.89 [1.78, 2.02] | 59.5 (1.25) | 59.1 [58.5, 61.7] |
| 12% | 1.77 (0.107) | 1.82 [1.65, 1.88] | 56.3 (0.870) | 56.2 [55.5, 57.8] |
| 14% | 1.83 (0.0776) | 1.86 [1.73, 1.91] | 58.0 (1.24) | 57.8 [56.3, 59.7] |
| 16% | 1.90 (0.0715) | 1.91 [1.81, 1.97] | 56.9 (1.54) | 57.4 [54.8, 58.7] |

Table 1 shows exemplary compression and yield strengths for various embodiments including cylinders fabricated by vat photopolymerization from a biocompatible photopolymer resin blend doped with various wt/wt precents of gentamicin. The range of compressive modulus for the exemplary embodiments is from about 1.1 to about 2.03 GPa, with an average compressive strength of about 1.81 GPa. The range of yield strength for the exemplary embodiments is from about 52.6 to about 61.3 MPa, with an average compressive strength of about 57.4 MPa.

TABLE 2

| | Tension | | |
|---|---|---|---|
| % Gentamicin | Average Peak Stress (MPa) | Average Young's Modulus (MPa) | Average Strain at Break (%) |
| 0% | 47.835 | 2247.367 | 14.07522 |
| 1% | 47.776 | 2329.286 | 9.580265 |
| 2% | 47.75 | 2477.599 | 5.968114 |
| 4% | 47.83375 | 2360.322 | 5.070027 |
| 6% | 46.4755 | 2360.982 | 4.284491 |
| 10% | 44.621 | 2381.869 | 4.132251 |

Table 2 shows exemplary tensile strengths for various embodiments including cylinders fabricated by vat photopolymerization from a biocompatible photopolymer resin blend doped with various wt/wt precents of gentamicin. The range of the average ultimate tensile strength for the exemplary embodiments is from about 44 to about 47 MPa. The range of the average Young's Modulus for the exemplary embodiments is from about 2360 MPa to about 2500 MPa. The range of the average strain at break for the exemplary embodiments is from about 4 to about 9%.

Materials created from the process described herein may have a wide variety of uses. In particular embodiments, the processes described herein may be beneficial in any application wherein a microbial infection is treated. Such as for example, periprosthetic joint infection (PJI). In particular embodiments, the processes described herein may be beneficial in any application wherein a pain reliever medicine is needed or chemotherapeutic. This example may be applicable for temporary knee or hip replacements or intermedullary or other internal fracture fixation devices.

CONCLUSION

The foregoing description of the exemplary embodiments has been presented only for the purposes of illustration and description is not intended to be exhaustive or to limit the devices, systems, methods, and apparatuses herein to the precise forms disclosed. Many modifications and variations are possible considering the above teachings.

The embodiments were chosen and described in order to explain the principles of the technology discussed herein and their practical application to enable others skilled in the art to utilize the various embodiments and with various modifications as are suited to the particular use contemplated. Alternative embodiments will become apparent to those skilled in the art to which the present technologies pertain without departing from their spirit and scope.

What is claimed is:

1. A method for producing a temporary medical implant comprising:
    pulverizing at least one therapeutic agent into a fine powder, then sifting and isolating the fine powder to attain therapeutic agent particles with a particle size distribution of less than 50 microns;
    creating a non-solid blend of a polymer and the therapeutic agent particles comprising between about 0.1 and about 20.0 weight percent of the therapeutic agent, wherein the weight percent is relative to a total weight of the non-solid blend;
    homogenizing the non-solid polymer blend via an immersion blender or homogenizer such that the therapeutic agent particles are distributed substantially evenly throughout the non-solid polymer blend;
    vat polymerizing the non-solid polymer blend containing at least one therapeutic agent to produce a therapeutic agent-eluting implant comprising the at least one therapeutic agent homogeneously distributed throughout the therapeutic agent-eluting implant; and
    cleaning and curing the therapeutic agent-eluting implant to produce a final device that supports physiologic loads when implanted within the patient, wherein:
    the therapeutic agent comprises of one or more of the following:
    antibiotic, antifungal, analgesic, or chemotherapeutic;
        the polymer comprises: 50-70 weight % of esterification products of 4,4'-isopropylidenediphenol, ethoxylated and 2-methylprop-2-enoic acid, 25-45 weight % of urethane dimethacrylate, 7-10 weight % of methacrylate monomer(s), and <2% of photoinitiator(s);
        the polymer has an initial boiling point/range of >100° C., a closed cup flash point of >93.5° C., a density of 1.09 g/cm$^3$, a dynamic viscosity of 1350 cps at 25° C., and is not flammable;
        the therapeutic agent-eluting implant comprises a gyroid structure;
        the therapeutic agent-eluting implant comprises an arthroplasty spacer; and
        the therapeutic agent-eluting implant comprises a compressive yield stress greater than or equal to 50 MPa, an ultimate tensile strength of greater than or equal to 20 MPa, and a Compressive Modulus of greater than or equal to 1000 MPa.

* * * * *